(12) United States Patent
Hiemer et al.

(10) Patent No.: US 7,537,735 B2
(45) Date of Patent: May 26, 2009

(54) ASPIRATOR SYSTEMS HAVING AN ASPIRATOR TIP OPTICAL LEVEL DETECTOR AND METHODS FOR USING THE SAME

(75) Inventors: Todd Hiemer, Edmond, OK (US); Paul Ratke, Edmond, OK (US)

(73) Assignee: Biomerieux, Inc., Durham, NC (US)

( * ) Notice: Subject to any disclaimer, the term of this patent is extended or adjusted under 35 U.S.C. 154(b) by 840 days.

(21) Appl. No.: 10/851,724

(22) Filed: May 21, 2004

(65) Prior Publication Data

US 2005/0257612 A1 Nov. 24, 2005

(51) Int. Cl.
  *G01N 35/10* (2006.01)
  *B01L 3/02* (2006.01)
(52) U.S. Cl. ............... 422/100; 422/106; 422/107; 422/108; 436/180; 73/863.32; 73/864.01; 73/864.02
(58) Field of Classification Search ............ 422/100
See application file for complete search history.

(56) References Cited

U.S. PATENT DOCUMENTS

| | | | |
|---|---|---|---|
| 3,683,196 A * | 8/1972 | Obenhaus | 250/227.11 |
| 3,995,167 A | 11/1976 | Kulig | 250/577 |
| 4,038,650 A | 7/1977 | Evans et al. | |
| 4,477,190 A | 10/1984 | Liston et al. | 356/418 |
| 4,764,671 A | 8/1988 | Park | 250/227 |
| 4,846,003 A | 7/1989 | Marquiss | |
| 4,880,971 A | 11/1989 | Danisch | 250/227 |
| 4,950,885 A | 8/1990 | Kershaw | 250/227.25 |
| 4,989,452 A | 2/1991 | Toon et al. | 73/293 |
| 5,059,812 A | 10/1991 | Huber | |

(Continued)

FOREIGN PATENT DOCUMENTS

DE 3113248 A1 10/1982

(Continued)

OTHER PUBLICATIONS

International Search Report and Written Opinion of the International Searching Authority for International patent application PCT/US2005/00671 mailed on Jun. 22, 2005.

*Primary Examiner*—Jill Warden
*Assistant Examiner*—P. Kathryn Wright
(74) *Attorney, Agent, or Firm*—Myers Bigel Sibley & Sajovec (57) ABSTRACT

Aspirator systems include an aspirator body member having a fluid passageway extending therein and a first and second optical conductor configured to receive and/or transmit light therethrough. A drive mechanism may be coupled to the aspirator body member and configured to move the aspirator body member between an advanced position and a retracted position. An aspirator tip is coupled to the aspirator body member at an end of the fluid passageway and having a fluid passageway therein extending from the end of the fluid passageway of the aspirator body member when coupled to the aspirator body member, the aspirator tip being coupled to the first and second optical conductors and comprising an optically transmissive material. A controller detects contact of the aspirator tip with a fluid based on a level of light received from the aspirator tip through at least one of the first and second optical conductors and determines a level of the fluid based on a position of the aspirator body member when contact of the aspirator tip with the fluid is detected.

11 Claims, 4 Drawing Sheets

U.S. PATENT DOCUMENTS

| | | | |
|---|---|---|---|
| 5,084,614 A | 1/1992 | Berkner | 250/227.11 |
| 5,267,474 A | 12/1993 | Ten Hoven | 73/290 R |
| 5,271,734 A | 12/1993 | Takeuchi | 433/72 |
| 5,271,902 A * | 12/1993 | Sakka et al. | 422/100 |
| 5,439,449 A | 8/1995 | Mapes et al. | 604/164 |
| 5,452,619 A | 9/1995 | Kawanabe et al. | 73/864.01 |
| 5,777,221 A | 7/1998 | Murthy et al. | 73/149 |
| 5,882,194 A | 3/1999 | Davis et al. | 433/29 |
| 5,897,509 A | 4/1999 | Toda et al. | 600/587 |
| 5,969,620 A | 10/1999 | Okulov | 433/29 |
| 6,100,094 A * | 8/2000 | Tajima | 436/54 |
| 6,158,269 A | 12/2000 | Dorenkott et al. | |
| 6,280,187 B1 | 8/2001 | Slone | 433/29 |
| 6,321,164 B1 | 11/2001 | Braun et al. | 702/22 |
| 6,396,584 B1 * | 5/2002 | Taguchi et al. | 356/436 |
| 6,602,072 B2 | 8/2003 | Burney | 433/96 |
| 2004/0072367 A1 * | 4/2004 | Ding et al. | 436/180 |
| 2005/0181519 A1 * | 8/2005 | Karg et al. | 436/180 |

FOREIGN PATENT DOCUMENTS

| | | |
|---|---|---|
| DE | 3248409 | 6/1984 |
| EP | 0 488 761 A2 | 6/1992 |
| EP | 0 866 336 A1 | 9/1998 |

\* cited by examiner

ASPIRATOR SYSTEMS HAVING AN ASPIRATOR TIP OPTICAL LEVEL DETECTOR AND METHODS FOR USING THE SAME

FIELD OF THE INVENTION

The present invention relates to devices for aspirating and detecting a level of fluids and, more particularly, to aspirator systems with optical level detection.

BACKGROUND OF THE INVENTION

Aspirator systems are used in a variety of applications, such as automated test apparatus where tests are run on samples of a fluid, such as a blood sample. In such test apparatus, it may be necessary to serially and automatically dispense and/or evacuate test samples, reagents and the like from various containers. During such tests, it is sometimes desired to measure an amount of a sample in a container. An example of such an automated test apparatus are described, for example, in U.S. Pat. No. 6,321,164, entitled "Method and Apparatus for Predicting the Presence of an Abnormal Level of One or More Proteins in the Clotting Cascade."

Various approaches are known for sensing the presence, level and/or other characteristics of fluids. A variety of principles may be used to measure fluid level and/or other characteristics. One such approach is ultrasonic measurement. Another is using capacitance as used in a capacitance type sensor. Optical sensors may also be used.

SUMMARY OF THE INVENTION

According to embodiments of the present invention, aspirator systems include an aspirator body member having a fluid passageway extending therein and a first and second optical conductor configured to receive and/or transmit light therethrough. A drive mechanism coupled to the aspirator body member is configured to move the aspirator body member between an advanced position and a retracted position. An aspirator tip is coupled to the aspirator body member at an end of the fluid passageway and has a fluid passageway therein extending from the end of the fluid passageway of the aspirator body member when coupled to the aspirator body member. The aspirator tip is coupled to the first and second optical conductors. The aspirator tip may be an optically transmissive material. A controller coupled to the aspirator tip is configured to detect contact of the aspirator tip with a fluid based on a level of light received from the aspirator tip through at least one of the first and second optical conductors and to determine a level of the fluid based on a position of the aspirator body member when contact of the aspirator tip with the fluid is detected.

In further embodiments of the present invention, the aspirator tip is a disposable tip removably coupled to the aspirator body member. The aspirator tip may be configured to be automatically removed from the aspirator body member by the aspirator system.

In some embodiments of the present invention, the aspirator system includes a light source optically coupled to the first optical conductor and a light detector circuit optically coupled to the second optical conductor that outputs a detected light level signal. The controller may be configured to detect contact of the aspirator tip with a fluid based on the detected light level signal. The first and second optical conductors may be light pipes and the aspirator tip may include a first and a second light pipe port, respectively, coupled to the first and second optical conductors of the aspirator body member. The first and second optical conductors may be optical fibers coupled to the aspirator body member.

In further embodiments of the present invention, a position detector is coupled to the controller and is configured to output a position signal corresponding to the location of the aspirator body member to the controller. The position detector may be a motor encoder coupled to the drive mechanism and the position signal may be an encoder count. The light detector circuit may be configured to distinguish light received directly from the light source and light reflected from an outer surface of the aspirator tip based on respective amplitudes thereof.

In certain embodiments of the present invention, the aspirator tip is configured to conduct light from the first optical conductor to an outer surface thereof and to conduct reflected light from the outer surface thereof to the second optical conductor. The aspirator tip may be a longitudinally extending, substantially cylindrical member having a tapered tip on a longitudinal end thereof displaced from the aspirator body member. The fluid passageway of the aspirator tip may extend longitudinally from the aspirator body member to the tapered tip of the aspirator tip and the fluid passageway of the aspirator tip may change diameter in the tapered tip. The aspirator tip may have at least one external diameter change discontinuity thereon and the detected light level signal may change when the at least one external diameter change discontinuity contacts the fluid.

In further embodiments of the present invention, methods for detecting a level of a fluid in a container in an aspirator system include dispensing the fluid into the container. An aspirator tip is moved toward the fluid in the container in a gaseous atmosphere while the aspirator system detects an amount of light provided to the aspirator tip that is reflected back through the aspirator tip to an optical detector from an outer surface of the aspirator tip and while detecting a position of the aspirator tip. Contact with the fluid is detected when the amount of light detected changes by a selected amount. The position of the aspirator tip is determined when contact with the fluid is detected to thereby detect the level of the fluid. The aspirator tip may be a removable aspirator tip and detecting contact with the fluid may be followed by removing the aspirator tip from an aspirator body member and installing a different aspirator tip on the aspirator body member. Contact with a different fluid sample is detected using the different aspirator tip. The aspirator body member may be part of an automated test apparatus and removing the aspirator tip and installing the different aspirator tip may be automatically performed by the test apparatus between tests of different fluid samples and/or types by the test apparatus.

In other embodiments of the present invention, methods o in an automated test apparatus of testing a test sample dispensed into a sample container in the apparatus. A level of the test sample in the container is determined by moving an aspirator tip towards the sample in the container in a gaseous atmosphere while detecting an amount of light provided to the aspirator tip that is reflected back through the aspirator tip to an optical detector from an outer surface of the aspirator tip and while detecting a position of the aspirator tip. Contact with the sample is determined when the amount of light detected changes by a selected amount and the position of the aspirator tip is determined when contact with the sample is detected to determine the level of the sample. A reagent is added to the sample container. A portion of the sample is evacuated (withdrawn) from the container with the aspirator tip.

A level of a remaining portion of the sample in the container is determined after evacuating a portion of the sample. The aspirator tip is moved towards the remaining portion of the sample in the container in a gaseous atmosphere while detecting an amount of light provided to the aspirator tip that is reflected back through the aspirator tip to an optical detector from an outer surface of the aspirator tip and while detecting a position of the aspirator tip. Contact with the remaining portion of the sample is determined when the amount of light detected changes by a selected amount. The position of the aspirator tip is determined when contact with the remaining portion of the sample is detected to detect the level of the remaining portion of the sample.

In further embodiments of the present invention, adding a reagent, evacutating a portion and determining a level are repeated for at least one additional reagent. Determining a level of a remaining portion of the sample may be followed by automatically removing the aspirator tip from an aspirator body member to which the aspirator tip is removably coupled in the test apparatus and automatically installing a different aspirator tip on the aspirator body member. Dispensing a test sample into a sample container in the apparatus, determining a level of the test sample in the container, adding a reagent to the sample container, evacuating a portion of the sample from the container with the aspirator tip and determining a level of a remaining portion of the sample in the container after evacuating a portion of the sample may be repeated for a different test sample using the different aspirator tip.

In other embodiments of the present invention, aspirator systems include an aspirator body member having a fluid passageway extending therein and a first and second optical conductor configured to receive and/or transmit light therethrough. A removable aspirator tip is coupled to the aspirator body member at an end of the fluid passageway and has a fluid passageway therein extending from the end of the fluid passageway of the aspirator body member when coupled to the aspirator body member. The aspirator tip is coupled to the first and second optical conductors and is an optically transmissive material. The aspirator tip is configured to reflect a first portion of light received from the first optical conductor light back through the aspirator tip to the second optical conductor from an outer surface of the aspirator tip when the outer surface is in contact with a gaseous atmosphere and a second portion of the light received from the first optical conductor, different from the first portion, when the outer surface is in contact with a fluid.

In further embodiments of the present invention, aspirator systems include an aspirator body member having a fluid passageway extending therein and a first and second optical conductor configured to receive and/or transmit light therethrough. A drive mechanism is coupled to the aspirator body member and configured to move the aspirator body member between an advanced position and a retracted position. A detachable aspirator tip is removably coupled to the aspirator body member at an end of the fluid passageway and has a fluid passageway therein extending from the end of the fluid passageway of the aspirator body member when coupled to the aspirator body member. The aspirator tip includes optical conductors thereon removably coupled to the first and second optical conductor of the aspirator body member respectively. A controller coupled to the aspirator tip is configured to detect contact of the aspirator tip with a fluid based on a level of light received from the aspirator tip through at least one of the first and second optical conductors and to determine a level of the fluid based on a position of the aspirator body member when contact of the aspirator tip with the fluid is detected.

BRIEF DESCRIPTION OF THE DRAWINGS

The accompanying drawings, which form a part of the specification, illustrate embodiments of the present invention. The drawings and description together serve to fully explain the invention. In the drawings.

DETAILED DESCRIPTION

The present invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. In the drawings, like numbers refer to like elements throughout. The terms "upwardly", "downwardly", "vertical", "horizontal", "bottom", "top" and the like are used herein for the purpose of explanation only.

As will be described further herein, various embodiments of the present invention may use a disposable aspirator tip, which incorporates a light pipe into the tip itself, to determine a level of a fluid in a container. The aspirator tip may be removed and replaced between sample runs, for example, to mitigate cross-contamination and/or to prevent other items from being added to a sample on the inside of a container, such as a cuvette. The use of disposable optics in the aspirator tip for level sensing may beneficially provide for fluid level detection through contact with only a single sample, which may help eliminate cross-contamination between samples and subsequent runs. Such may be particularly useful for testing biological samples, such as, but not limited to, blood or plasma samples. The aspirator tip may be configured to use a change in the index of refraction between a gas and the fluid sample being measured to change the amount of light reflected from an outer surface of the tip, back up the tip. As such, when the tip contacts the fluid, the reflected light intensity may change. Various approaches may be taken to calculate a level of the fluid based on detection of the point of contact as will be understood by those of skill in the art.

Figure 1:
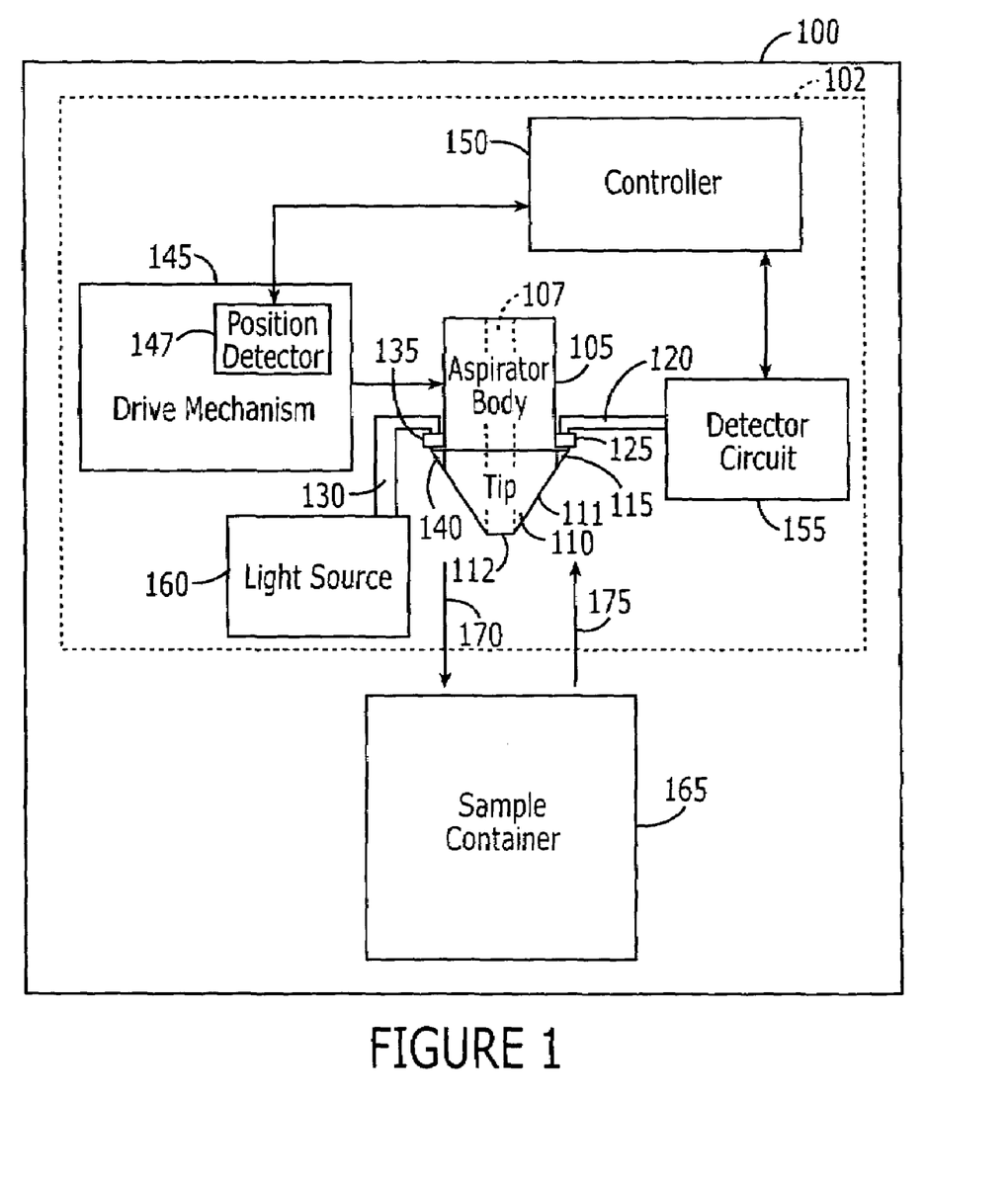
FIG. 1 is a schematic block diagram illustrating a test apparatus including an aspirator system in accordance with some embodiments of the present invention.

Referring now to FIG. 1, a test apparatus 100 including an aspirator system 102 according to some embodiments of the present invention will now be further described. The test apparatus 100 of FIG. 1 is illustrated schematically including a schematic illustration of features, components and/or aspects of an aspirator system 102 that may be used in accordance with various embodiments of the present invention. It will be understood that the test apparatus 100 will generally include various other features, components and/or aspects related to the particular tests performed by the test apparatus 100, which other aspects are generally known and will not be further described herein except as they may relate to the aspirator systems of the present invention.

The aspirator system 102 of the embodiments of FIG. 1 is configured to measure the level of a fluid sample in the sample container 165. In addition to measuring the level of the fluid sample, in various embodiments of the present invention the aspirator system 102 may be configured to add and/or evacuate fluid samples to/from the sample container 165 and/or other containers in the test apparatus 100, such as other sample containers, reagent containers and the like, and to move fluids between respective ones of such containers based on the requirements of a test being performed on the test apparatus 100. Accordingly, the aspirator systems of the present invention may perform various conventional operations of known aspirator systems, which conventional aspects will not be further described herein except as they relate to various embodiments of the present invention.

As shown in the embodiments of FIG. 1, the aspirator system 102 includes an aspirator body member 105 and an aspirator tip 110 coupled to the aspirator body member 105. The aspirator system 102 may further include a drive mechanism 145 coupled to the aspirator body member 105 and a controller 150, which may be operatively coupled to the aspirator tip 110 through the detector circuit 155. The detector circuit 155 may include an optical detector that detects reflected light from the aspirator tip 110 through the optical conductor 120. A light source 160 may be optically coupled to the aspirator tip 110 through the optical conductor 130.

The aspirator body member 105 may have a fluid passageway 107 extending therein for delivering a sample to and/or evacuating/removing a sample from the sample container 165 and/or other containers and/or channels associated with the test apparatus 100. The optical conductors 120, 130 shown in FIG. 1 can be coupled to the aspirator body 105 by connectors 125, 135 to receive and/or transmit light therethrough. While shown as distinct optical (light) pipes/fibers in FIG. 1, the optical conductors 120, 130 in other embodiments of the present invention may route light internally through the aspirator body 105 rather than being attached to an outer surface of the aspirator body 105. In any event, the optical conductors 120, 130 associated with the aspirator body 105 are configured to provide light to and/or receive reflected light from the aspirator tip 110.

The aspirator tip 110 is coupled to the aspirator body 105 at an end of the fluid passageway 107. The aspirator tip 110 is shown as including a fluid passageway 112 therein that extends from the end of the fluid passageway 107 when the aspirator tip 110 is coupled to the aspirator body 105 to provide a continuous fluid passageway through the aspirator body 105 and tip 110. The aspirator tip 110 may be optically coupled to the optical conductors 120, 130, for example, by the light pipe ports 115, 140. The aspirator tip 110 may be an optically transmissive material to allow transmission of light therethrough and may be a disposable tip removably coupled to the aspirator body 105. In particular, the test apparatus 100 and the aspirator tip 110 may be configured to allow the aspirator system 102 to automatically remove and replace the aspirator tip 110, for example, between test cycles and/or on different test samples and/or the like.

In particular embodiments of the present invention, the aspirator tip 110 is configured to detect contact with a fluid sample based on a change in an index of refraction of a fluid contacting an outer surface thereof causing a different amount of internal refraction of light then when the aspirator tip 110 is in a gaseous atmosphere, such as air. The aspirator tip 110 may be configured to conduct light from the optical conductor 130 to an outer surface 111 of the aspirator tip 110 and to conduct reflected light from the outer surface 111 of the aspirator tip 110 to the optical conductor 120. Thus, a first portion of the light from the optical conductor 130 may be reflected back to the optical conductor 120 when the outer surface of the aspirator tip 110 is in contact with a gaseous atmosphere and a second, different portion of the light from the optical conductor 120 may be reflected back through the aspirator tip 110 when the aspirator tip 110 outer surface is in contact with a fluid sample in the sample container 165.

The drive mechanism 145, in some embodiments of the present invention, is configured to automatically move the aspirator body member 105 between an advanced position and a retracted position. As illustrated in FIG. 1, movement toward the sample container 165 in the direction of arrow 170 corresponds to movement to the advanced position and movement away from the sample container 165 in the direction of arrow 175 corresponds to movement to the retracted position. The drive mechanism 145 may also be configured to provide for movement in other directions associated with different aspects of an automated test cycle of the test apparatus 100.

For the illustrated embodiments of FIG. 1, a position detector 147 is associated with the drive mechanism 145. The position detector 147 is illustrated as coupled to the controller 150 to output a position signal to the controller 150 that corresponds to a location of the aspirator body member 105, either in absolute terms and/or relative to another reference point in the test apparatus, such as the sample container 165. In some embodiments of the present invention, the position detector 147 is a motor encoder coupled to the drive mechanism 145, in which case, the position signal to the controller 150 may be an encoder count. However, other types of position detectors, including those providing direct detection of the position of the aspirator body member 105, for example, by optical, magnetic and/or electro-mechanical sensors, are also suitable for use with various embodiments of the present invention. Accordingly, while shown in association with the drive mechanism 145 in the embodiments of FIG. 1, the position detector 147 need not be associated with the drive mechanism 145.

The controller 150 may be configured to detect contact of the aspirator tip 110 with a fluid in the sample container 165 based on a level of light received from the aspirator tip 110 through the optical conductor 120. As illustrated in the embodiments of FIG. 1, the amount of light received by the optical conductor 120 is detected by the light detector circuit 155. For example, the light detector circuit 155 may be configured to distinguish light received directly from the light source 160 and light reflected from an outer surface of the aspirator tip, 10 based on respective amplitudes thereof. The light detector circuit 155 may output a detected light level signal to the controller 150, based on which the controller 150 may determine when contact with a fluid occurs. Alternatively, the light detector circuit 155 may be configured to detect contact with the fluid itself based on the level of light received from the optical conductor 120 and then send a fluid contact signal to the controller 150 rather than an output signal proportional to the amount of light detected. In yet other embodiments of the present invention, the detector circuit 155 may be implemented as part of the controller 150 and the controller 150 may be directly coupled to the optical conductor 120. In any event, the controller 150 may then determine a level of a fluid sample in the sample container 165 based on a position of the aspirator body member 105, including the aspirator tip 110 coupled thereto, when contact of the aspirator tip 110 with the fluid sample is detected.

Figure 2A:
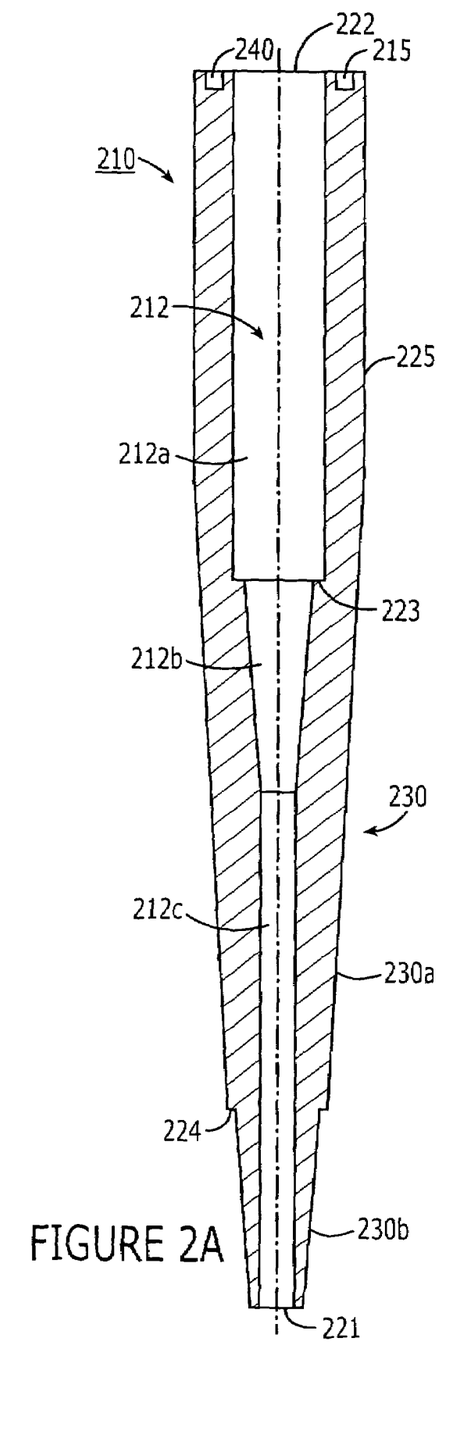
FIG. 2A is a cross-sectional side view illustrating an aspirator tip according to some embodiments of the present invention.
Figure 2B:
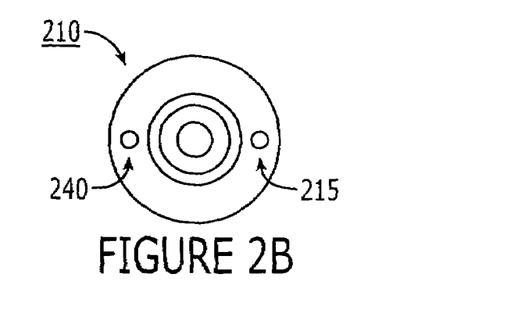
FIG. 2B is a top view of the aspirator tip of FIG. 2A.
Figure 2C:
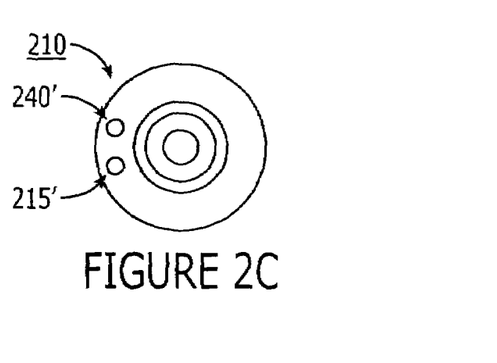
FIG. 2C is a top view of an aspirator tip in accordance with other embodiments of the present invention.

Further embodiments of the present invention will now be described with reference to FIGS. 2A through 2C. FIG. 2A is a side cross-sectional view of an aspirator tip 210 according to some embodiments of the present invention. FIGS. 2B and 2C are top views of the aspirator tip 210 illustrating alternative coupling locations for optical conductors to the aspirator tip 210. As shown in FIG. 2A, the aspirator tip 210 is a longitudinally extending, generally cylindrical member having an upper body portion 225 and a tapered lower body portion 230. The lower body portion 230 for the embodiments of FIG. 2A is divided into a first part 230a and a second part 230b by an external diameter change discontinuity 224. The external diameter change discontinuity may provide a change in the detected light level when it contacts a fluid. As such, for the embodiments of FIG. 2A, it may be possible to detect both the initial contact of the second part 230b with the fluid and when the second part 230b is fully inserted into the fluid. The external diameter change discontinuity 224 is illustrated as a stepped outer surface in FIG. 2A. However, the discontinuity may take a variety of other forms, such as angled or curved surfaces, providing a change in detected light level.

A fluid passageway 212 extends through the aspirator tip 210. The fluid passageway 212 includes an upper part 212a having a first diameter, a lower part 212c having a second, smaller diameter and a tapered part 212b therebetween. The passageway 212 extends through the aspirator tip 210 from a first end 222 configured to couple to the aspirator body member 105 and a second end 221 including an opening in the aspirator tip 210 for receiving fluid from and/or dispensing fluid into the sample container 165. The fluid passageway 212 changes diameter as it extends through the tapered lower body portion 230, both due to the tapered part 212b and, for the illustrated embodiments, due to the internal diameter change discontinuity 223.

FIGS. 2A through 2C also illustrate various embodiments of light pipe ports 215, 240 in the aspirator tip 210. The light pipe ports 215, 240 may be positioned at various circumferential locations on the first end 222 of the aspirator tip 210. As shown in FIG. 2B, the respective ports 215, 240 are positioned on opposite sides displaced at about 180° from each other. As shown in FIG. 2C, in other embodiments of the present invention, the light pipe ports 215, 240 may be positioned substantially adjacent each other.

In particular embodiments of the present invention, the aspirator tip 210 may have an overall length of about 1.735 inches. The upper body member 225 may have a length of about 0.55 inches and a diameter of about 0.5 inches. The passageway 212 may have a diameter at the first end 222 of about 0.28 inches and a minimum diameter at the opposite end thereof of about 0.09 inches. The inner diameter step discontinuity 223 may drop the passageway diameter from about 0.28 inches to about 0.23 inches. The minimum outer diameter of the aspirator tip 210 at the second end 221 thereof may be about 0.14 inches. And the external diameter discontinuity 224 may be positioned about 0.295 inches from the end 221 longitudinally. The inner diameter step discontinuity 223 may be positioned about 0.675 inches from the first end 222 longitudinally. The tapered portion 212b of the passageway 212 may extend longitudinally about 0.36 inches.

In some embodiments of the present invention, optical fibers may be integrally attached, for example, in an adhesive manner (such as tape or glue), by molding and/or by ultrasonic welding to the aspirator tip 110, 210 rather than or in addition to providing the aspirator tip 110 itself as an optically transmissive member to act as a light pipe. The aspirator tip 110 may still be detachable in such embodiments by providing for detachment of the optical fibers from the tip and/or aspirator body member 105 as well. If cross-contamination is a problem for a particular application, the attached optical fibers may be decoupled from the aspirator body member and different optical fibers associated with a different aspirator tip may then be coupled to the aspirator body member.

Figure 3:
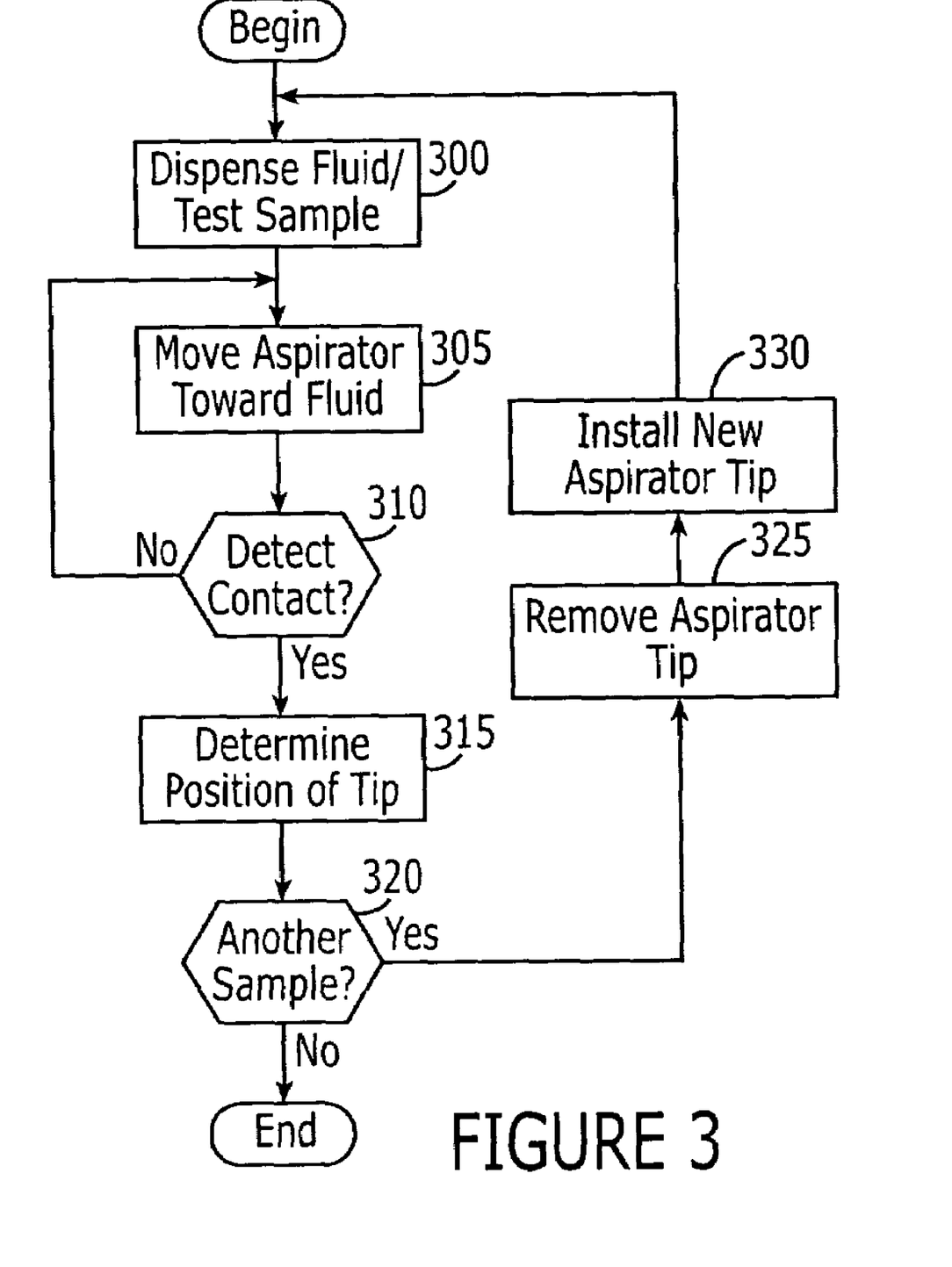
FIG. 3 is a flowchart illustrating operations for detecting a level of a fluid in a container in accordance with some embodiments of the present invention.

Referring now to the flow chart illustration of FIG. 3, various embodiments of methods for detecting a level of a fluid in a container in an aspirator system will now be described. Operations begin at Block 300 with dispensing of the fluid into the container. An aspirator tip is moved towards the fluid in a container in a gaseous atmosphere while detecting an amount of light provided to the aspirator tip that is reflected back through the aspirator tip to an optical detector from an outer surface of the aspirator tip (Block 305). The position of the aspirator tip is also detected while moving the aspirator tip. Contact with the fluid is detected when the amount of light detected changes by a selected amount (Block 310). The aspirator tip continues to move towards the fluid until contact is detected at Block 310. The position of the aspirator tip is determined when contact with the fluid is detected to detect the level of fluid (Block 315).

In some embodiments of the present invention, the aspirator tip is a removable aspirator tip and, if a different fluid sample is to be detected (Block 320), the previously used aspirator tip can be removed from the aspirator body member of the aspirator system (Block 325). A different aspirator tip is installed on the aspirator body member (Block 330). Operations may then return to Block 300 through 315 to detect contact with the different fluid sample using the different aspirator tip so as to determine a level of the different fluid sample in the container. The aspirator body member may be part of an automated test apparatus and operations related to removing the aspirator tip and installing the different aspirator tip at Blocks 325 and 330 may be automatically performed by the test apparatus between tests of different fluid samples by the test apparatus and/or at other desired intervals for replacing the aspirator tip. Note that, as used herein, a "different" aspirator tip may be an identical or distinct tip design and may be a new or re-used tip, for example, a cleaned and re-cycled tip.

Figure 4:
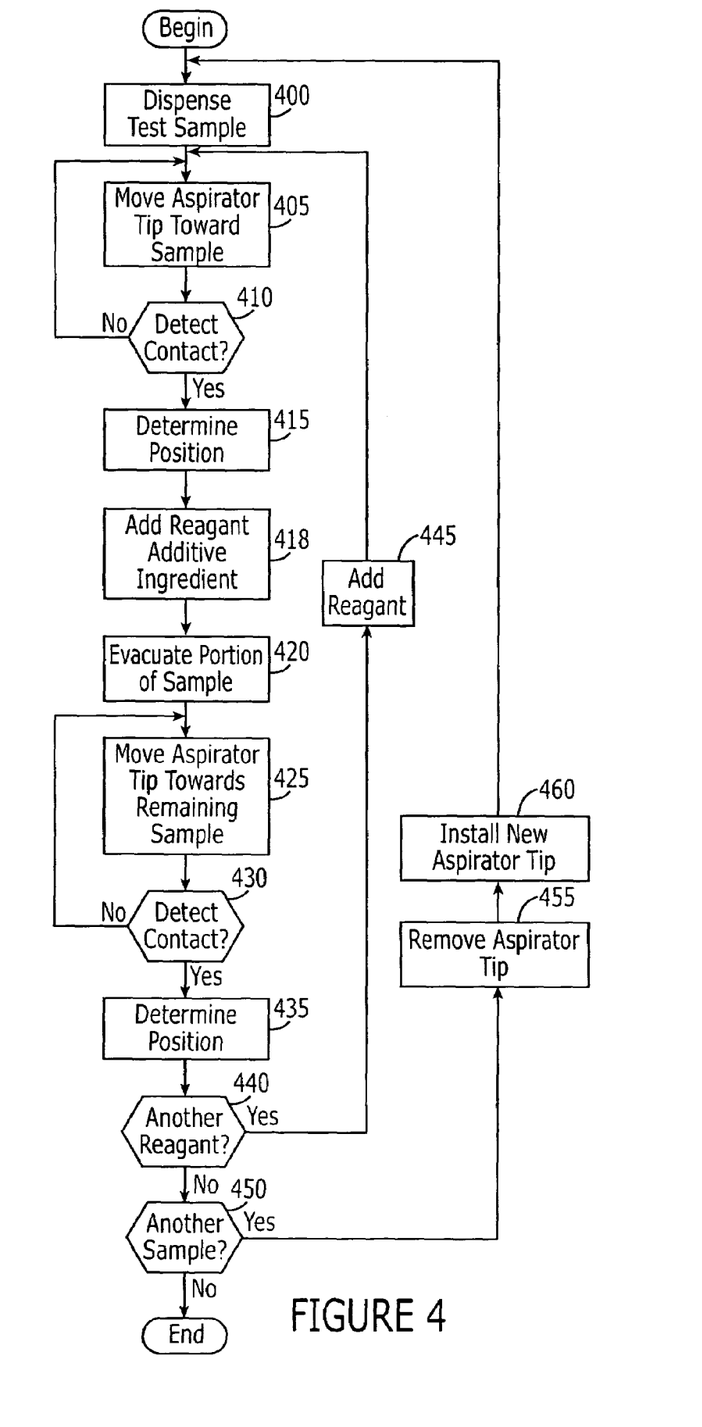
FIG. 4 is a flowchart illustrating operations for testing a sample in an automated test apparatus in accordance with some embodiments of the present invention.

Operations for testing a sample in an automated test apparatus according to various embodiments of the present invention will now be further described with reference to the flow chart illustration of FIG. 4. As shown in FIG. 4, operations begin at Block 400 by dispensing a test sample into a sample container in the apparatus. A level of the test sample in the container is then determined as will now be described with reference to Blocks 405 through 415. An aspirator tip is moved toward the sample in the container in a gaseous atmosphere while detecting an amount of light provided to the aspirator tip that is reflected back through the aspirator tip to an optical detector from an outer surface of the aspirator tip and while detecting a position of the aspirator tip (Block 405). Operations at Block 405 continue until contact with the sample is detected when the amount of light detected changes by a selected amount (Block 410). The position of the aspirator tip is determined when contact with the sample is detected to determine the level of the sample (Block 415).

A reagent and/or other desired additive ingredient is added to the sample container including the dispensed test sample (Block 418). Subsequently, a portion of the sample is evacuated from the container using the aspirator tip (Block 420).

After evacuation of a portion of the sample, a level of a remaining portion of the sample in the container is determined as will now be described with reference to Blocks 425 through 435. The aspirator tip is moved towards the remaining portion of the sample in the container in a gaseous atmosphere while detecting an amount of light provided to the aspirator tip that is reflected back through the aspirator tip to an optical detector from an outer surface of the aspirator tip (Block 425). A position of the aspirator tip is detected during movement of the aspirator tip at Block 425. Movement continues until contact of the aspirator tip with the remaining portion of the sample is detected when the amount of light detected changes by a selected amount (Block 430). The position of the aspirator tip is determined when contact with the remaining portion of the sample is detected to detect the level of the remaining portion of the sample (Block 435).

In some embodiments of the present invention, the test of a sample in the automated test apparatus includes test protocols requiring different reagents and/or other desired additive ingredient(s) to be mixed with the sample. Accordingly, in such embodiments, if another reagent is to be used in the test (Block 440), the reagent is added (Block 445) and operations return to Block 405.

In further embodiments of the present invention, the test apparatus may test additional test samples where it is desired to avoid cross contamination being introduced by the aspirator tip. In such embodiments, when an additional sample is to be tested (Block 450), the aspirator tip may be automatically removed from the aspirator body member to which the aspirator tip is removably coupled in the test apparatus (Block 455). A new aspirator tip may be automatically installed on the aspirator body member (Block 460). Operations may then return to Block 400 and the sequence of operations described previously may be repeated on the different test sample.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

What is claimed is:

1. An aspirator system comprising:
   an aspirator body member having a fluid passageway extending therein and a first and second optical conductor configured to receive and/or transmit light therethrough;
   drive mechanism coupled to the aspirator body member and configured to move the aspirator body member between an advanced position and a retracted position;
   an aspirator tip coupled to the aspirator body member at an end of the fluid passageway and having a fluid passageway therein extending from the end of the fluid passageway of the aspirator body member when coupled to the aspirator body member, the aspirator tip being coupled to the first and second optical conductors and comprising an optically transmissive material and being configured to conduct light from the first optical conductor to an outer surface of the aspirator tip and to conduct reflected light from the outer surface thereof to the second optical conductor, wherein the aspirator tip comprises a longitudinally extending, generally cylindrical member having a tapered tip on a longitudinal end thereof displaced from the aspirator body member;
   a controller operatively coupled to the aspirator tip that is configured to detect contact of the aspirator tip with a fluid based on a changed level of light received from the aspirator tip through at least one of the first and second optical conductors responsive to a change of an index of refraction at the outer surface of the aspirator tip when the outer surface of the aspirator tip contacts the fluid and to determine a level of the fluid based on a position of the aspirator body member when contact of the aspirator tip with the fluid is detected;
   a light source optically coupled to the first optical conductor; and
   a light detector circuit optically coupled to the second optical conductor that outputs a detected light level signal, wherein the controller is configured to detect contact of the aspirator tip with a fluid based on the detected light level signal,
   wherein the fluid passageway of the aspirator tip includes at least one internal diameter change discontinuity and/or the aspirator tip has at least one external diameter change discontinuity thereon and wherein the detected light level signal changes when the at least one external diameter change discontinuity and/or the at least one internal diameter change discontinuity contacts the fluid.

2. The aspirator system of claim 1 wherein the aspirator tip is a disposable tip removably coupled to the aspirator body member.

3. The aspirator system of claim 2 wherein the aspirator tip is configured to be automatically removed from the aspirator body member by the aspirator system.

4. The aspirator system of claim 1 wherein the first and second optical conductors comprise light pipes and wherein the aspirator tip includes a first and a second light pipe port respectively coupled to the first and second optical conductors of the aspirator body member.

5. The aspirator system of claim 1 wherein the first and second optical conductors comprise optical fibers coupled to the aspirator body member.

6. The aspirator system of claim 1 further comprising a position detector coupled to the controller that outputs a position signal corresponding to the location of the aspirator body member to the controller.

7. The aspirator system of claim 6 wherein the position detector comprises a motor encoder coupled to the drive mechanism and wherein the position signal comprises an encoder count.

8. The aspirator system of claim 1 wherein the fluid passageway of the aspirator tip includes the at least one internal diameter change discontinuity.

9. The aspirator system of claim 1 wherein the aspirator tip includes the at least one external diameter change discontinuity thereon and wherein the detected light level signal changes when the at least one external diameter change discontinuity contacts the fluid.

10. The aspirator system of claim 1 wherein the light detector circuit is configured to distinguish light received directly from the light source and light reflected from the outer surface of the aspirator tip based on respective amplitudes thereof.

11. An aspirator system comprising:

an aspirator body member having a fluid passageway extending therein and a first and second optical conductor configured to receive and/or transmit light therethrough;

a drive mechanism coupled to the aspirator body member and configured to move the aspirator body member between an advanced position and a retracted position;

a detachable aspirator tip removably coupled to the aspirator body member at an end of the fluid passageway and having a fluid passageway therein extending from the end of the fluid passageway of the aspirator body member when coupled to the aspirator body member, the aspirator tip including optical conductors thereon removably coupled to the first and second optical conductor of the aspirator body member respectively and comprising an optically transmissive material configured to conduct light from the first optical conductor to an outer surface of the aspirator tip and to conduct reflected light from the outer surface thereof to the second optical conductor, wherein the aspirator tip comprises a longitudinally extending, generally cylindrical member having a tapered tip on a longitudinal end thereof displaced from the aspirator body member;

a controller coupled to the aspirator tip that is configured to detect contact of the aspirator tip with a fluid based on a changed level of light received from the aspirator tip through at least one of the first and second optical conductors responsive to a change of an index of refraction at the outer surface of the aspirator tip when the outer surface of the aspirator tip contacts the fluid and to determine a level of the fluid based on a position of the aspirator body member when contact of the aspirator tip with the fluid is detected;

a light source optically coupled to the first optical conductor; and a light detector circuit optically coupled to the second optical conductor that outputs a detected light level signal, wherein the controller is configured to detect contact of the aspirator tip with a fluid based on the detected light level signal, wherein the fluid passageway of the aspirator tip includes at least one internal diameter change discontinuity and/or the aspirator tip has at least one external diameter change discontinuity thereon and wherein the detected light level signal changes when the at least one external diameter change discontinuity and/or the at least one internal diameter change discontinuity contacts the fluid.

* * * * *